(12) United States Patent
Mole et al.

(10) Patent No.: US 7,604,774 B2
(45) Date of Patent: Oct. 20, 2009

(54) STERILIZATION AND DECONTAMINATION

(75) Inventors: Alan Mole, Worcestershire (GB); John Percival Burleigh Golding, Halifax (GB)

(73) Assignee: Steritrox Limited, Cheshire (GB)

( * ) Notice: Subject to any disclaimer, the term of this patent is extended or adjusted under 35 U.S.C. 154(b) by 453 days.

(21) Appl. No.: 10/895,888

(22) Filed: Jul. 22, 2004

(65) Prior Publication Data
US 2005/0031486 A1 Feb. 10, 2005

(30) Foreign Application Priority Data
Jul. 22, 2003 (GB) .................. 0317059.4

(51) Int. Cl.
*A61L 2/16* (2006.01)
(52) U.S. Cl. .................. 422/28; 422/120; 422/123; 422/186.07
(58) Field of Classification Search .................. 422/120, 422/123, 186.07, 28
See application file for complete search history.

(56) References Cited

U.S. PATENT DOCUMENTS

2004/0022679 A1 * 2/2004 St. Onge et al. .............. 422/62

FOREIGN PATENT DOCUMENTS

| DE | 42 13 778 | 5/1993 |
| EP | 1223387 A2 * | 7/2002 |
| GB | 1 278 043 | 6/1972 |
| GB | WO 03/028773 | 6/1972 |
| JP | 2002-360675 | 12/2002 |
| WO | WO 03/001119 | 1/2003 |
| WO | WO 03/038351 | 5/2003 |

* cited by examiner

*Primary Examiner*—Sean E Conley
(74) *Attorney, Agent, or Firm*—Young & Thompson

(57) ABSTRACT

A method of sterilization and decontamination comprises the steps of producing a humidified environment having a relative humidity which is higher than ambient humidity; discharging ozone into the humidified environment; and then introducing an aromatic hydrocarbon into the humidified environment to preferentially react with the discharged ozone to form hydroxyl radicals. Apparatus is also provided for use with the method.

7 Claims, 2 Drawing Sheets

STERILIZATION AND DECONTAMINATION

BACKGROUND OF THE INVENTION

1. Field of the Invention

This invention relates to a method of sterilisation and decontamination, and to apparatus for use with said method.

2. Description of the Related Art

It is a requirement to quickly and effectively sterilise and sanitise enclosed spaces, such as kitchen areas, to destroy potentially harmful microorganisms, such as bacteria and viruses, contaminating the air and surfaces therewithin.

The biocidal activity of ozone is widely known and appreciated, and it is also known that the provision of ozone in a humid atmosphere increases the biocidal effectiveness.

However, problems associated with the use of ozone as a biocide have been the relatively lengthy post-treatment process to ensure that the environment is safe for returning occupants, the use of potentially environmentally damaging chemicals during the process, the general ineffectiveness of the process in sanitising the environment, and the overall lack of simplicity of quickly setting up and using the apparatus.

The present invention seeks to provide a solution to these problems.

SUMMARY OF THE INVENTION

According to a first aspect of the present invention, there is provided a method of sterilisation and decontamination, said method comprising steps of:

a) producing a humidified environment having a relative humidity which is higher than ambient humidity;
b) discharging ozone into said humidified environment; and
c) introducing an aromatic hydrocarbon into said humidified environment to preferentially react with said discharged ozone to form hydroxyl radicals.

Preferable and/or optional features of the first aspect of the invention are set forth in claims 1 to 7, inclusive.

According to a second aspect of the present invention, there is provided sterilisation and decontamination apparatus comprising a humidifier unit, an ozone discharge unit, an aromatic hydrocarbon discharge unit, and a controller by which said humidifier unit, said ozone discharge unit and said aromatic hydrocarbon discharge unit are controllable based on ambient conditions.

The invention will now be more specifically described, by way of example only, with reference to the accompanying drawings.

DESCRIPTION OF THE PREFERRED EMBODIMENT

Figure 1:
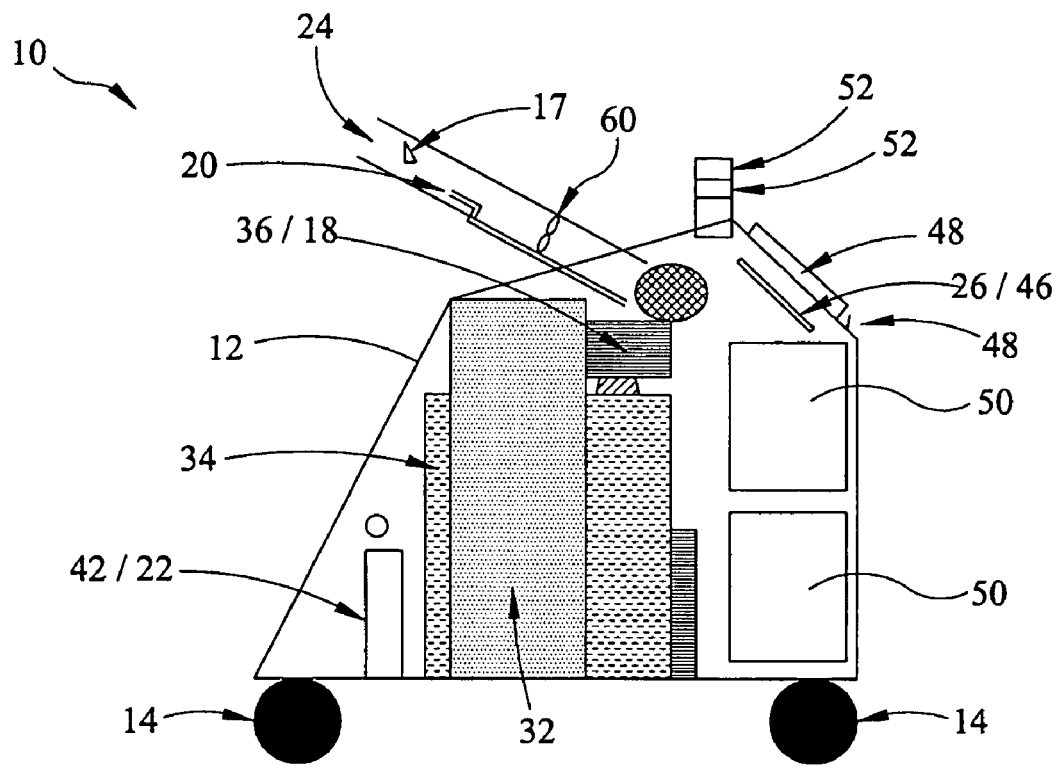
FIG. 1 is a diagrammatic elevational view of one embodiment of sterilisation and decontamination apparatus, in accordance with the second aspect of the invention.
Figure 2:
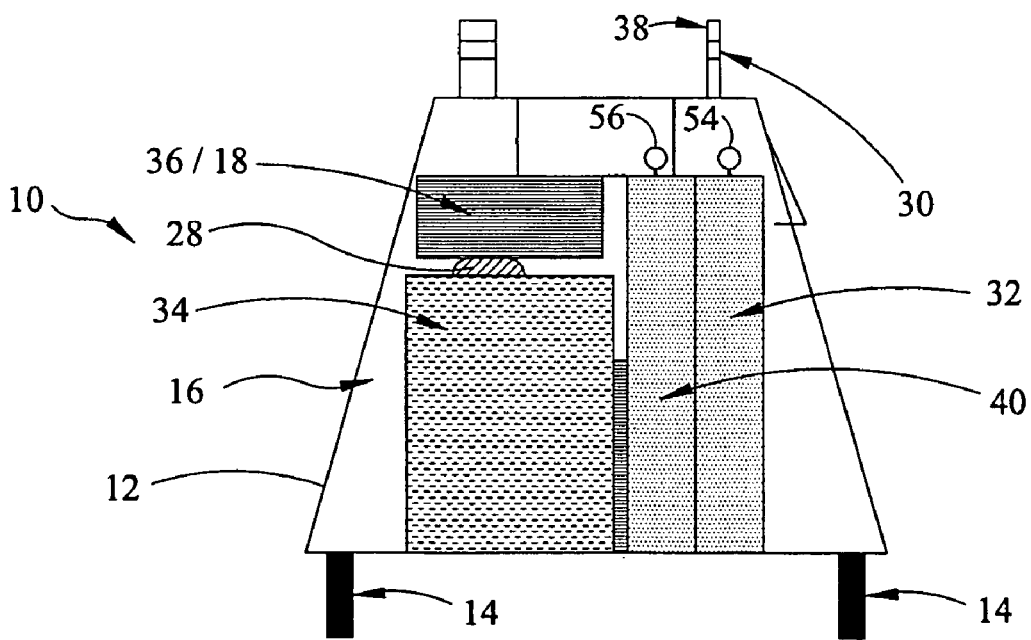
FIG. 2 is a diagrammatic front view of the apparatus shown in FIG. 1.
Figure 3:
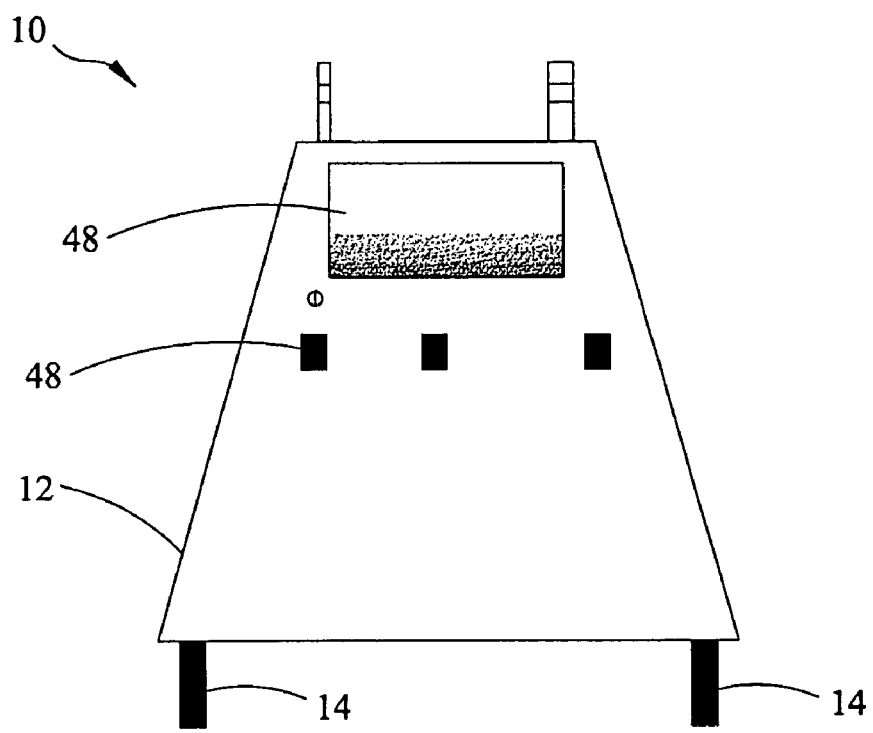
FIG. 3 is a diagrammatic view of one exterior surface of the apparatus.
Figure 4:
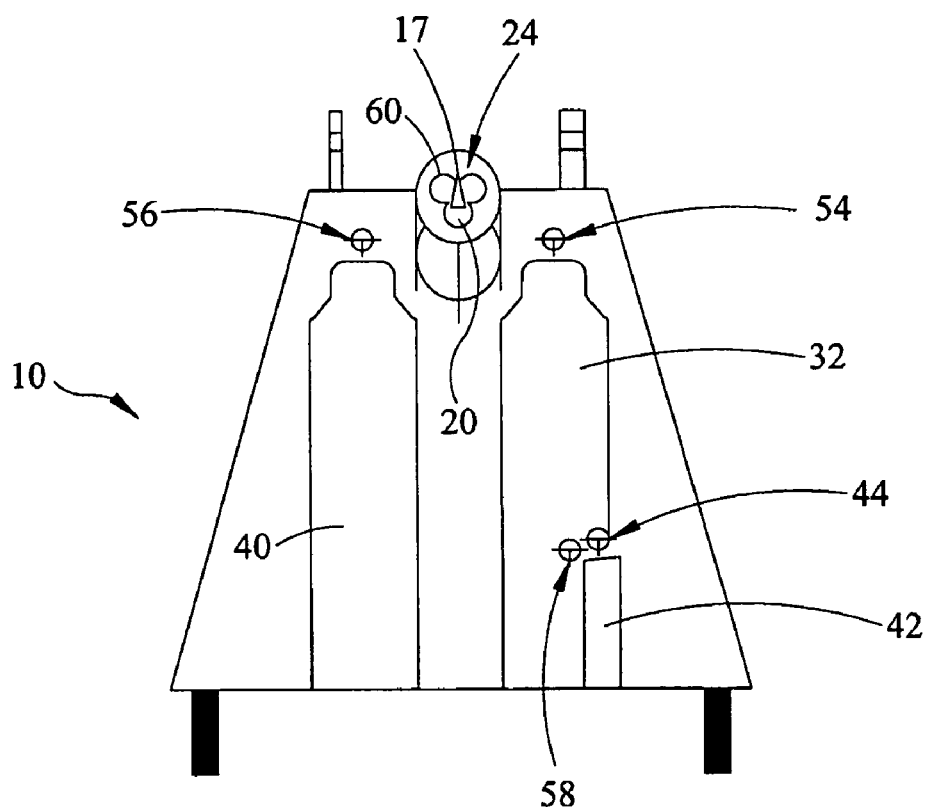
FIG. 4 is a diagrammatic view of another exterior surface of the apparatus.

Referring now to the drawings, there is shown sterilisation and decontamination apparatus 10 comprising a portable enclosure 12 which is openable and which, in use, generates a positive pressure within the interior. The enclosure 12 has wheels 14 and houses a humidifier unit 16 having a humidified air outlet 17, an ozone discharge unit 18 having an ozone discharge outlet 20 on the exterior of the enclosure 12, a hydrocarbon discharge unit 22 having a hydrocarbon discharge outlet 24 on the exterior of the enclosure 12, and a control unit 26.

The humidifier unit 16 includes an ultrasonic humidifier 28, a humidistat sensor 30, a compressed air supply 32, and a water reservoir 34. The compressed air supply 32, in this embodiment, is in the form of a compressed air tank or container housed within the enclosure 12. The compressed air tank is connected to the water reservoir 34 and the humidifier 28.

The ozone discharge unit 18 includes an ozone generator 36, an ozone detector sensor 38, and an oxygen supply 40 for supplying oxygen to the ozone generator 36.

The hydrocarbon discharge unit 22 includes a hydrocarbon supply 42 in the form of a tank or container containing a gaseous volatile aromatic hydrocarbon, such as butene or a natural olefin, such as Terpene. Specifically, the butene is trans-2-butene. However, the hydrocarbon can be any suitable aromatic hydrocarbon having a carbon-carbon double bond, for reasons which will become apparent hereinafter. The hydrocarbon is selected based on its speed of reaction with ozone.

The hydrocarbon tank includes a pressure sensor 44 for monitoring the pressure of the gas in the tank.

The control unit 26 controls the apparatus 10 and is preset with at least one sterilisation and decontamination routine. The control unit 26 includes a controller 46 and a user interface 48 by which a user can input commends to the apparatus 10.

The apparatus 10 may include an on-board battery 50 and/or may be connectable to a mains power supply. In the case of the on-board battery 50, the battery is preferably rechargeable.

The apparatus 10 will also typically include other safety features, such as one or more motion detectors (not shown). If exterior movement within the area of the apparatus is detected at any time during operation of the apparatus 10, the controller 46 will abort any operation and provide a suitable indication using, for example, warning lights 52.

In use, the apparatus 10 is first located in the area which is to be sterilised and decontaminated. The power to the apparatus 10 is switched on, and the control unit 26 undertakes an initial safety check comprising checking the pressure level of the hydrocarbon supply 42, checking the ambient relative humidity, and checking for the presence of people in the vicinity via the motion detectors. If the safety check is not passed, the apparatus 10 does not operate and outputs a suitable indication using warning lights 52.

Providing the safety check is passed, if the relative humidity is less than 75% at ambient temperature, the controller 46 operates a compressed air valve 54 of the compressed air supply 32 and compressed air is supplied to the water reservoir 34 at, typically, 15 psi and to the humidifier 28 at, typically, 75 psi. The water in the water reservoir 34 is forced by the compressed air into the humidifier 28, where it is atomised by the compressed air at 75 psi. Following sonification by the ultrasonic humidifier 28, it is discharged into the ambient surroundings from the humidifier 28 through the humidifier outlet 17.

The humidified air is output at a temperature which is above the ambient dew point of the environment, and is thus non-condensing.

The controller 46 continues to monitor the ambient humidity through the humidistat sensor 30. If after a predetermined interval, for example 10 minutes, the required relative humidity level has not been reached, the controller 46 aborts the sterilisation and decontamination routine and provides a suitable indication.

Once the relative humidity reaches 75% or greater, the controller 46 operates an oxygen supply valve 56 of the oxygen supply 40, and the ozone generator 36. Oxygen is thus supplied to the ozone generator 36, and ozone is generated. The generated ozone is then fed into the discharging humidified airstream containing water droplets of less than 10 microns. The controller 46 provides a suitable indication that the ozone generator 36 is operating, and monitors the ambient ozone levels through the ozone detector sensor 38.

If after a predetermined interval, for example 10 minutes, the ozone detector sensor 38 fails to monitor at least 10 ppm of ozone, the controller 46 determines that the area is not sufficiently sealed or that an error has occurred and aborts the sterilisation and decontamination routine. The controller 46 also outputs a suitable indication that the routine has been aborted.

The ozone level to be detected is settable, enabling elimination of certain types of bacteria/viruses while leaving others. However a typical setting is 10 ppm, and once the preset ozone level has been detected within the allotted interval, the controller 46 enters a timing phase.

The timing phase is also presettable, for example, to one hour, but will depend on the room volume to be treated and the type of decontamination/sterilisation to be provided.

During the timing phase, the ozone concentration and relative humidity are continuously monitored. If the ozone level falls below a predetermined threshold, for example 9 ppm, the ozone discharge unit 18 is reactivated to replenish the ozone levels. If the humidity falls below a predetermined threshold, for example 75%, the humidifier unit 16 is reactivated to increase the relative humidity to 75% or greater.

Again, during the reactivation period, if either the ozone concentration or the relative humidity fails to reach the abovementioned predetermined minimums within a set interval, for example 10 minutes, the controller 46 aborts the sterilisation and decontamination routine and outputs a suitable indication.

After the timing phase has elapsed, the controller 46 closes the compressed air valve 54 and the oxygen supply valve 56, and the humidifier unit 16 and the ozone discharge unit 18 are switched off. The controller 46 then operates a hydrocarbon discharge valve 58 of the hydrocarbon discharge unit 22 to discharge the aromatic hydrocarbon into the ambient environment. The aromatic hydrocarbon is provided to a concentration of no more than 20 ppm, and preferentially reacts with the residual ozone to accelerate the breakdown of the ozone to the hydroxyl radicals. The introduction of the hydrocarbon results in a free radical cascade. The hydrocarbon is provided in excess to ensure complete removal of the ozone, thereby offering faster user re-entry to the treated area.

When the ozone detector sensor 38 detects that the ozone concentration levels are less than a predetermined value, for example 0.2 ppm or less, the controller 46 closes the hydrocarbon discharge valve 58 and outputs an indication that the sterilisation and decontamination routine is complete. The ozone level of 0.2 ppm, depending on the size of the area being sterilised and decontaminated, is usually achieved within 3 to 4 minutes.

In very simplistic terms, the reactions that are followed are:

$$O_3 + H_2O = H_2O_2 + O_2 \xrightarrow{O_2 \uparrow} HO + OH \longrightarrow H_2O + O_2$$

(ozone)

and preferential reaction $$O_3 + HC = CH \xrightarrow{OH^-} H_2O + CO_2$$

(hydrocarbon)

However, the actual reaction varies depending on the hydrocarbon. Trans-2-butene forms weak acids, such as acetic acid, which then rapidly dissociates to carbon dioxide and water. Pollutants in the environment will also cross-react with the ozone and the hydroxyl radicals.

However, importantly, by use of a hydrocarbon, a complex reaction with zero vapour pressure results. As such, the reaction condenses on surfaces and particles, magnifying the biocidal activity of the process.

If the ozone detector sensor 38 does not indicate that the predetermined safe level of ozone has been reached within a predetermined interval, for example 10 minutes, the controller 46 outputs an indication warning of potentially hazardous ozone levels.

It is envisaged that the sterilisation and decontamination apparatus may be integrally formed as part of an area, or may be only partly portable. For example, the compressed air supply and/or oxygen supply could be integrally formed as part of the area to be regularly sterilised and decontaminated, instead of being housed within the enclosure of the apparatus. In this case, the or each supply would be linked to the apparatus via a releasably detachable umbilical pipe.

Although the oxygen supply is typically in the form of one or more oxygen tanks or cylinders, a commercially available oxygen concentrator can be used.

The apparatus uses an electric fan 60 as a gas movement device to circulate the ambient air, ozone and hydrocarbon. However, an air amplifier powered by the compressed air supply can be utilised as an alternate gas movement device. This is particularly advantageous where a fixed supply of compressed air is provided at a specific location. An air amplifier enables a reduction in the weight and complexity of the apparatus.

The above-described apparatus utilises a method of producing an artificially high level of non-condensing humidity, and generating in-situ a high concentration of ozone. The humidity has, typically, a 2 to 3 micron water droplet size.

The materials of the apparatus resist corrosive effects of ozone and the solvent effects of the hydrocarbon.

The condition of a the valves are monitored using integrally incorporated sensors connected to the controller. The valves failsafe to the closed position so that user safety is paramount at a times.

The controller may incorporate a tamper proof recording system to monitor use, time and date.

The or each preset routine may be remotely initiated by a user from outside the area to be sterilised and decontaminated.

The use of the aromatic hydrocarbon results in the production of relatively harmless by-products from the ozone, such as acetic acid which, being a weak acid, quickly dissociates to carbon dioxide and water but which itself acts as a mild biocide.

It is thus possible to provide a method which is fast and effective, and apparatus which is discrete and portable. The method provides better than 99.99% effective sterilisation and decontamination of an area without impacting the environment with harmful by-products. Rapid re-use of a contaminated area can thus be realised. The above-described method has proven to be lethal to a wide variety of pathogens, including bacteria such as Methicillin Resistant Staphylococcus Aureus (MRSA).

The embodiments described above are given by way of examples only, and other modifications will be apparent to persons skilled in the art without departing from the scope of the invention as defined by the appended claims.

What is claimed is:

1. A method of sterilisation and decontamination, said method comprising:
    a) producing a humidified environment and monitoring the humidity to determine that a relative humidity of at least 75% at ambient temperature has been reached;
    b) discharging ozone into said humidified environment and monitoring an ozone level within the environment;
    c) continuously monitoring the relative humidity and ozone concentration for a predetermined period of time to ensure the humidity and concentration levels are maintained at a predetermined minimum level; and
    d) after the predetermined period of time and continuous monitoring of a relative humidity and ozone concentration above a predetermined minimum level, halting the production of the humidified environment and discharge of ozone and introducing a gaseous volatile olefin into said humidified environment to preferentially react with said discharged ozone to form hydroxyl radicals.

2. A method as claimed in claim 1, wherein humidity produced in step (a) is non-condensing humidity.

3. A method as claimed in claim 1, wherein said olefin is provided in a quantity of no more than 20 ppm.

4. A method as claimed in claim 1, wherein said olefin is butene.

5. A method as claimed in claim 1, wherein said olefin is a natural olefin.

6. A method as claimed in claim 5, wherein said natural olefin is terpene.

7. A method of sterilisation and decontamination, which comprises:
    providing an apparatus comprising a humidifier unit, an ozone discharge unit, a hydrocarbon discharge unit, and a controller by which said humidifier unit, said ozone discharge unit and said hydrocarbon discharge unit are controllable based on ambient conditions;
    producing a humidified environment and monitoring the humidity to determine that a relative humidity of at least 75% at ambient temperature has been reached;
    discharging ozone into said humidified environment and monitoring an ozone level within the environment;
    continuously monitoring the relative humidity and ozone concentration for a predetermined period of time to ensure the humidity and concentration levels are maintained at a predetermined minimum level; and
    after the predetermined period of time and continuous monitoring of a relative humidity and ozone concentration above a predetermined minimum level, halting the production of the humidified environment and discharge of ozone and introducing a gaseous volatile olefin into said humidified environment to preferentially react with said discharged ozone to form hydroxyl radicals.

* * * * *

UNITED STATES PATENT AND TRADEMARK OFFICE
CERTIFICATE OF CORRECTION

| | |
|---|---|
| PATENT NO. | : 7,604,774 B2 |
| APPLICATION NO. | : 10/895888 |
| DATED | : October 20, 2009 |
| INVENTOR(S) | : Mole et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 694 days.

Signed and Sealed this

Fifth Day of October, 2010

David J. Kappos
*Director of the United States Patent and Trademark Office*